United States Patent [19]
Fischell et al.

[11] Patent Number: 5,735,859
[45] Date of Patent: Apr. 7, 1998

[54] DISTALLY ATTACHABLE AND RELEASABLE SHEATH FOR A STENT DELIVERY SYSTEM

[75] Inventors: Robert E. Fischell, Dayton, Md.; David R. Fischell, Fair Haven, N.J.; Tim A. Fischell, Richland, Mich.

[73] Assignee: Cathco, Inc., Dayton, Md.

[21] Appl. No.: 800,613

[22] Filed: Feb. 14, 1997

[51] Int. Cl.$^6$ ............................................. A61B 11/00
[52] U.S. Cl. ........................... 606/108; 606/198; 606/191
[58] Field of Search .................................. 606/191, 198, 606/108

[56] References Cited

U.S. PATENT DOCUMENTS

| | | | |
|---|---|---|---|
| 5,290,295 | 3/1994 | Querals et al. | 606/108 |
| 5,628,755 | 5/1997 | Heller et al. | 606/108 |

*Primary Examiner*—Michael Buiz
*Assistant Examiner*—Tina T. D. Pham

[57] ABSTRACT

The present invention is a device and method for securing and releasing the distal end of a thin-walled sheath to and from a distal section of a stent delivery catheter. The invention comprises a stent delivery catheter system which includes a sheath which is releasably attached to a distal section of a stent delivery catheter. When the stent delivery system has been advanced into the body so that the stent (which is situated coaxially within the sheath) is placed at the site of an arterial stenosis where it is to be deployed, the sheath is released from the stent delivery catheter and then the sheath is pulled back in a proximal direction thereby uncovering the stent. Self-deploying stents will automatically deploy when the sheath is pulled back. Balloon expandable stents can be deployed by balloon inflation after the sheath has been pulled back. One embodiment of the distally attachable and releasable sheath utilizes a guide wire that passes through the stent delivery catheter first to hold and then to release the distal end of the sheath from a distal section of the stent delivery catheter.

13 Claims, 4 Drawing Sheets

DISTALLY ATTACHABLE AND RELEASABLE SHEATH FOR A STENT DELIVERY SYSTEM

FIELD OF USE

This invention is in the field of catheters for delivering stents into a vessel of a human body.

BACKGROUND OF THE INVENTION

Intravascular stents are well known in the field of interventional cardiology for the treatment of arterial stenoses. When placed through the body's vascular system, most stents are mounted onto a balloon angioplasty catheter with or without a cylindrical sheath that covers the stent prior to stent deployment by balloon expansion at the site of a dilated stenosis. Self-expanding stents are almost always contained within a cylindrical sheath which is pulled back to release the stent. If a sheath is not used, the rough surface of the stent can damage or remove endothelial cells from the arterial wall as the outer surface of the stent rubs the inside walls of the curved coronary (or other) arteries. Without a sheath, the stent may also get caught on the guiding catheter during movement into or out of the body which can cause the stent to come off the delivery catheter and embolize into the vasculature. When a sheath is used, it can have a few disadvantages. A first disadvantage is that all prior art sheaths are secured only at the proximal end to the stent delivery catheter system. Therefore, in order to have a sufficient column strength, the sheath must be relatively thick-walled, making it stiff and bulky so that passage through tortuous coronary arteries can be difficult. Another disadvantage of prior art sheaths is that they have blunt distal ends which can be caught on an already deployed stent, a calcified piece of intimal dissected tissue or a tight stenosis. Still further, when secured only at the proximal end of a stent delivery catheter, the sheath often either uncovers the stent due to significant bending of the stent delivery catheter or the sheath advances too far distally beyond the distal end of the stent. Finally, because of the larger diameter, blunt end and stiffness of sheathed stent delivery systems or the rough outer surface of unsheathed stent delivery systems, predilatation with another balloon angioplasty catheter is almost always required before stent implantation.

SUMMARY OF THE INVENTION

The present invention is a means and method for securing a thin-walled sheath to the distal end of a stent delivery catheter. The invention comprises a stent delivery catheter system, which includes a sheath which is held in place near the distal end of the stent delivery catheter by the guide wire that passes through the stent delivery catheter. When the stent delivery system has been advanced into the body so that the stent (which is situated coaxially within the sheath) is placed at the site of an arterial stenosis where it is to be deployed, the guide wire is pulled back to release the sheath which can then be pulled back in a proximal direction uncovering the stent. Self-deploying stents will automatically deploy when the sheath is pulled back. Balloon expandable stents can be deployed by balloon inflation after the sheath has been pulled back.

Because during insertion through the vascular system, the sheath is secured firmly at its distal end and is free to move axially at its proximal end, any axial motion of the sheath relative to the stent delivery catheter will result in axial motion of the sheath's proximal fitting that lies outside of the patients body. This is no problem whatsoever. Thus, with a distally secured sheath, there is no risk of the stent becoming uncovered. With this design the sheath can never extend too far in either the proximal or distal direction relative to the stent.

Furthermore, since the sheath is secured to the stent delivery catheter at the sheath's distal end, the sheath can be made from a very thin-walled elastomer cylinder which provides a smaller outside diameter and more flexible distal section for the stent delivery catheter system as compared to prior art sheathed stent delivery systems. Still further, the sheath design presented herein has a highly tapered distal end which may be advantageous for insertion through previously deployed stents, tortuous vessels or tight stenoses. Such a flexible tapered and low profile delivery system might obviate the need for balloon predilatation of most stenoses. This is especially true because a distally attached sheath, unlike a proximally attached sheath, can add significantly to the pushability of the stent delivery catheter system so that the system's distal section can be pushed through an arterial stenosis.

Therefore, it is an object of this invention to have a highly flexible thin-walled sheath that is secured at its distal end to the distal end of a stent delivery catheter.

Another object of this invention is that the proximal end of the sheath is free to move in an axial direction as the stent delivery catheter system is advanced through the vascular system.

Another object of this invention is to have a sheath that can be secured to the delivery catheter at both proximal and distal ends of the sheath and delivery catheter so as to enhance the pushability of the stent delivery catheter system through an arterial stenosis.

Still another object of this invention is that after the stent on the stent delivery catheter has been positioned at the proper location within an arterial stenosis, the guide wire can be pulled back to release the sheath so that pulling back on the sheath's proximal end causes the stent to be uncovered thus allowing the stent to be deployed.

Yet another object of this invention is to have a sheathed stent delivery system whose tapered distal end and smooth outside surface and improved system pushability allows it to cross undilated stenoses so that stent delivery can be accomplished without a balloon predilatation step.

These and other objects of this invention will become obvious to persons of ordinary still in this art upon reading of the specification presented herein including the drawings as described below.

DETAILED DESCRIPTION OF THE DRAWINGS

Figures 1, 2, 3, 4:
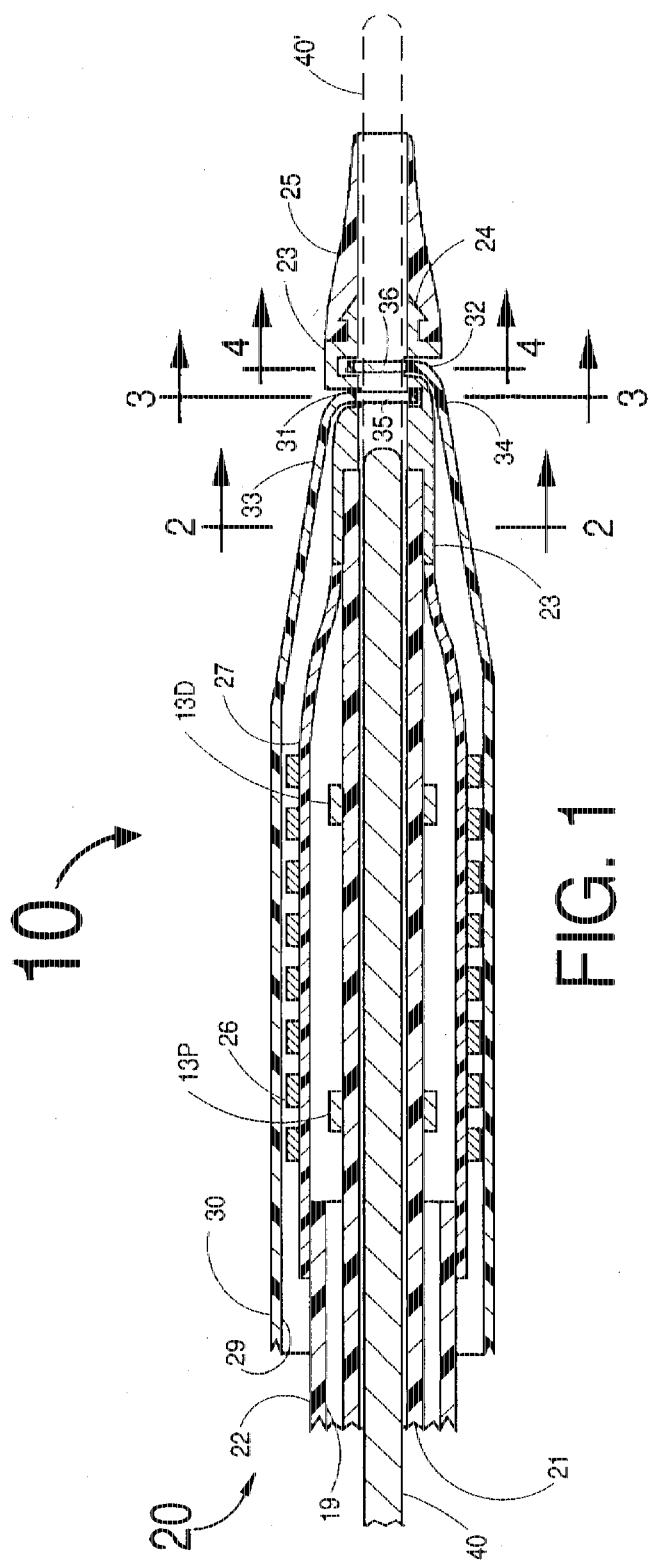
FIG. 1 is the longitudinal cross section of the distal section of the balloon expandable stent delivery catheter system which is a preferred embodiment of the present invention.
FIG. 2 is a transverse cross section of the stent delivery catheter system at section 2—2 of FIG. 1.
FIG. 3 is a transverse cross section of the stent delivery catheter system at section 3—3 of FIG. 1.
FIG. 4 is a transverse cross section of the stent delivery catheter system at section 4—4 of FIG. 1.

FIG. 1 is a longitudinal cross section of a distal section of the stent delivery catheter system 10 which consists of a stent delivery catheter 20, a stent 26, a sheath 30 and a guide wire 40. The stent delivery catheter 20 consists of an inner shaft 21, an outer shaft 22, a distal fitting 23 having a distal end 24 which is attached to a flexible elastomer tapered tip 25. The stent delivery catheter 20 also includes an inflatable balloon 27 that is attached at its proximal end to the outer shaft 22 and at its distal end to the inner shaft 21.

An annular passageway 19 that lies between the outer surface of the inner shaft 21 and the inner surface of the outer shaft 22 is used for inflating and deflating the balloon 27.

The stent delivery catheter 20 has a proximal radiopaque marker band 13P and a distal radiopaque marker band 13D which generally indicate the proximal and distal extremities of the stent 26 after the sheath 30 is pulled back to uncover the stent 26 and the balloon 27 is inflated to deploy the stent 26.

Figure 5:
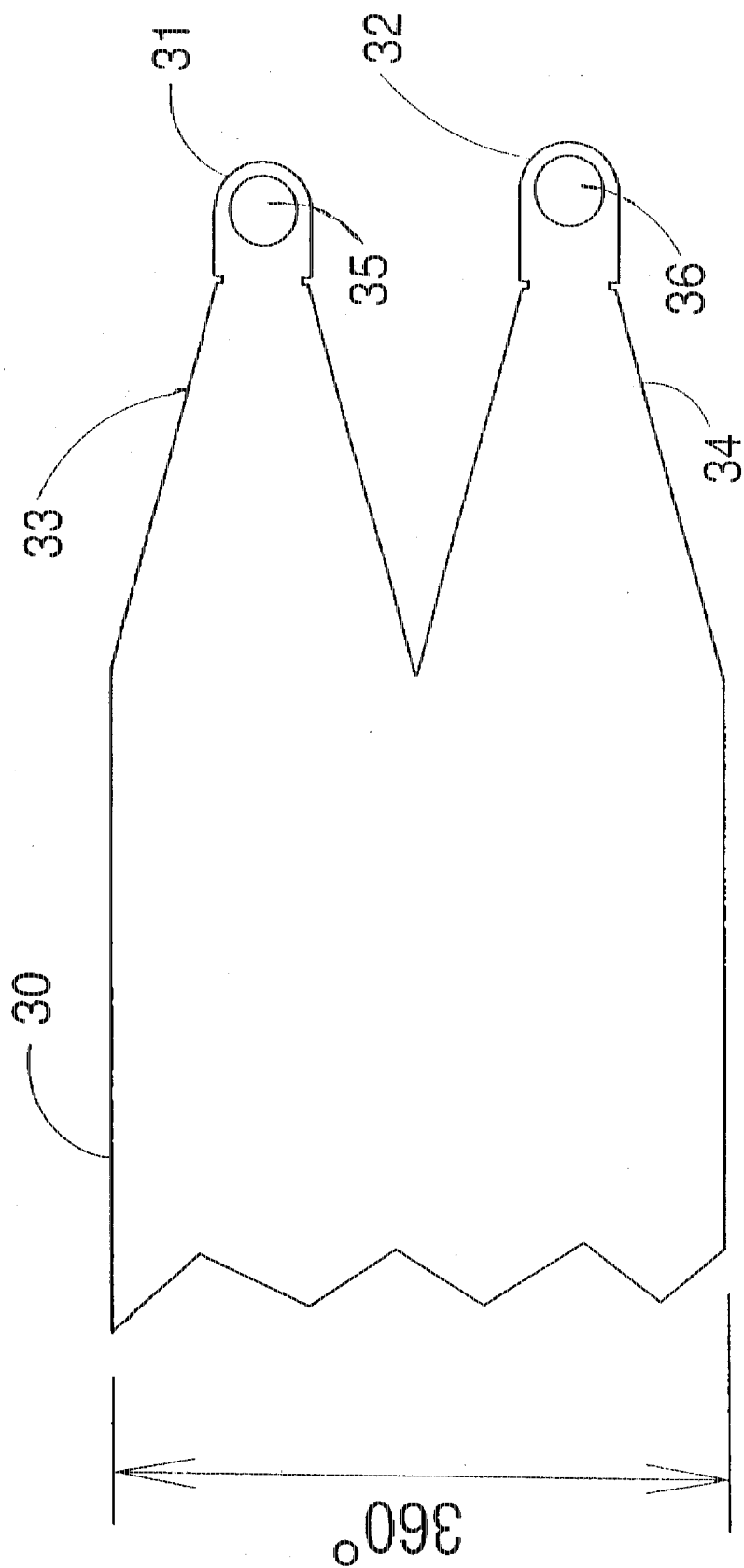
FIG. 5 is a flat, layout view of the distal section of the sheath.

As seen in FIGS. 2 and 5, the sheath 30 has a tapered distal section consisting of an upper tapered section 33 and a lower tapered section 34. The distal ends of the tapered sections 33 and 34 are, respectively, the foldable tabs 31 and 32 having central holes 35 and 36 through which the guide wire 40 can be passed. Thus for the typical guide wire 40 having an outside diameter of 0.014 inches, the holes 35 and 36 in the tabs 31 and 32 would typically have a diameter between 0.015 and 0.020 inches.

As seen in FIGS. 1, 3 and 4 the tabs 31 and 32 can be slid into slots in the distal fitting 23 as long as the distal end of the guide wire 40 lies proximal to the slots in the fitting 23. After the tabs 31 and 32 have been placed in the slots of the fitting 23, the guide wire 40 can be advanced distally through the holes 35 and 36 in the foldable tabs 31 and 32 as indicated by the dotted lines for the guide wire 40' thus firmly securing the distal end of the sheath 30 to the distal end of the stent delivery catheter 20. In this configuration, the stent delivery catheter system 10 is advanced through a patient's vascular system.

To prevent the tabs 31 and 32 from coming out of the distal fitting 23 during insertion of the guide wire 40' into the stent delivery catheter system 10 before a procedure, the stent delivery catheter system 10 would typically be packaged with a disposable wire and a clam shell cover. The disposable wire (not shown) would have been inserted from the distal end of the stent delivery catheter system 10, through the holes 35 and 36 in the tabs 31 and 32 of the sheath; and the removable clam shell cover (also not shown) would have been placed by the factory over the distal end of the sheath 30 to prevent the tabs 31 and 32 from coming out of the slots in the distal fitting 23 during insertion of the guide wire 40'. Before insertion into the human body, the disposable wire would be removed, the guide wire 40' would be inserted to hold the tabs 31 and 32 in place and the clam shell cover could then be removed before insertion of the stent delivery catheter system 10 into the patient's body.

Figure 6:
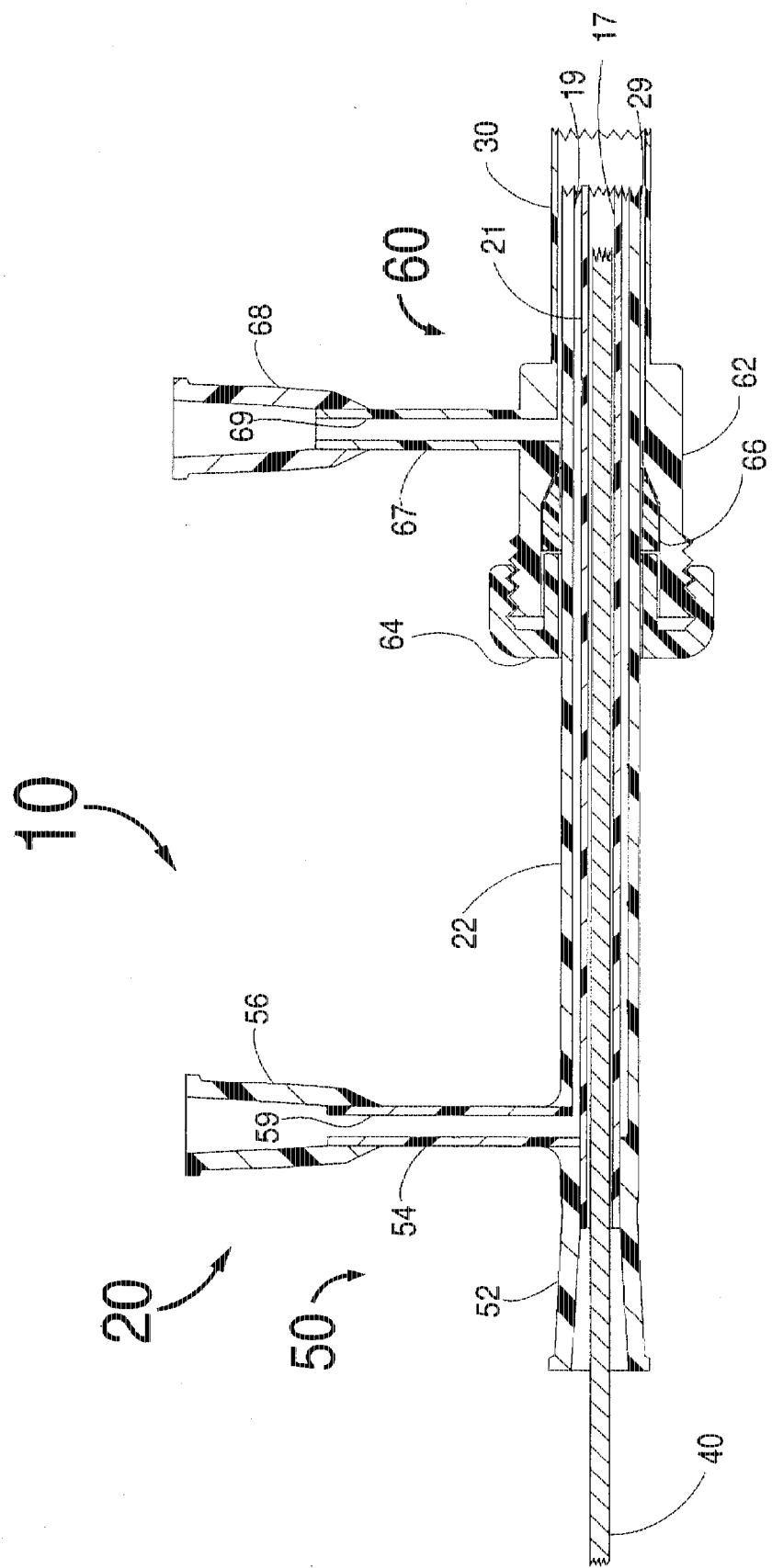
FIG. 6 is a longitudinal cross section of the proximal section of the stent delivery catheter system.

FIG. 6 illustrates a proximal section of the stent delivery catheter system 10. FIG. 6 shows that the stent delivery catheter 20 also includes (at the proximal end) an adapter fitting 50 having a Luer fitting 52 and a side arm 54 which has a Luer fitting 56. The side arm 54 has a central lumen 59 which is in fluid communication with the annular passageway 19 for the passage of fluid to inflate and deflate the balloon 27 of FIG. 1.

FIG. 6 also shows a Tuohy-Borst adaptor 60 having a main body 62 and a threaded nut 64 that can be screwed onto the main body 62 in order to seal the elastomer gland 66 against the outer surface of the outer shaft 22 thus preventing the back-flow of blood through the annular passageway 29 that lies between the cylindrical sheath 30 and the outer shaft 22. The Tuohy-Borst adaptor 60 also includes a side arm 67 having a Luer fitting 68 and a central lumen 69 for flushing out the annular passageway 29 prior to insertion of the stent delivery catheter system 10 into a patient's vascular system.

The method for operating the stent delivery catheter system 10 for placing the stent within any vessel of a human body would be as follows:

(a) With the guide wire 40' placed through the holes 35 and 36 in the tabs 31 and 32 of the sheath 30 and with the nut 64 made loose enough so that the Tuohy-Borst adaptor 60 can move slideably over the outer shaft 22 of the stent delivery catheter 20, the stent delivery catheter system 10 is advanced through the vascular system until the stent 26 is at a desired location.

(b) The guide wire 40' is pulled back until its distal end lies proximal to the tab 31.

(c) The Tuohy-Borst adaptor 60 is then pulled back relative to the fitting 50 which pulls the tabs 31 and 32 out of the slots in the distal fitting 23.

(d) The Tuohy-Borst adaptor 60 is pulled back still further until the distal end of the tabs 31 and 32 lie proximal to the proximal end of the stent 26.

(e) The balloon 27 is then inflated, thus deploying the stent 26 radially outward.

(f) The balloon 27 is then deflated and the stent delivery catheter system 10 is pulled out of the patient's body while leaving the deployed stent 26 in place against the vessel wall.

Figure 7:
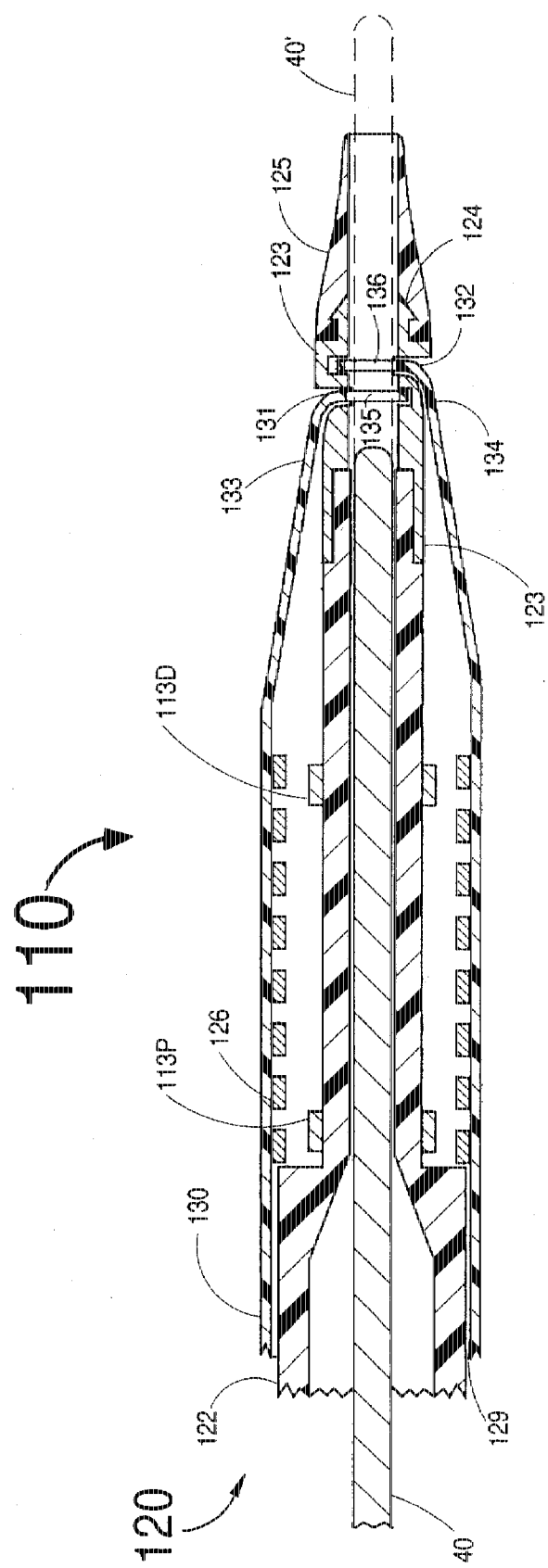
FIG. 7 is a longitudinal cross section of the distal section of an alternative embodiment of the present invention comprising a self-expanding stent delivery catheter system.

FIG. 7 is a longitudinal cross section of a distal section of an alternate embodiment of the present invention which is a stent delivery catheter system 100 which consists of a stent delivery catheter 120, a self-expanding stent 126, a sheath 130 and a guide wire 40. The stent delivery catheter 120 consists of a shaft 122, a distal fitting 123 having a distal end 124 which is attached to a flexible elastomer tapered tip 125.

The stent delivery catheter 120 has a proximal radiopaque marker band 113P and a distal radiopaque marker band 113D which generally indicate the proximal and distal extremities of the deployed self-expanding stent 126 after the sheath 130 is pulled back to release the stent 126.

The sheath 130 is the same shape as illustrated by the sheath 30 in FIG. 5. In this embodiment the sheath 130 has a tapered distal section consisting of an upper tapered section 133 and a lower tapered section 134. The distal ends of the tapered sections 133 and 134 are, respectively, the foldable tabs 131 and 132, having central holes 135 and 136 through which the guide wire 40 can be passed.

Although FIGS. 1 through 7, inclusive, illustrate an "over-the-wire" types of catheters for delivering an expandable stent, it should be understood that this invention of a guide wire releasable sheath could also be used with a "rapid exchange" type of the stent delivery catheter in which the guide wire would exit from the stent delivery catheter near its distal end proximal to the stent location. This would require a slot in the sheath also proximal to stent location through which the exiting guide wire might pass.

The materials of the stent delivery catheter system 10 and 110 are well known in the art of devices for intervention cardiology. Typically, all elastomer parts could be made from elastomers such as polyurethane, polyethylene, PTFE, FEP, or any similar plastic. The distal-fitting 23 is ideally machined from a high density metal such as tantalum or it could be molded from a hard plastic such as polycarbonate. Furthermore it should be understood that this concept of a guide wire releasable sheath would also be workable if the sheath had only one tab at its distal end through which the guide wire would be placed. Still further it would be highly advantageous to provide a lubricity coating to both the elastomer tapered tips 25 and 125 and the outer surface of the sheaths 30 and 130.

Although this invention can utilize a guide wire to release the distal end of the sheath from a distal section of the stent delivery catheter, it is also envisioned that other methods could be used both with or without guide wire pullback for releasing the sheath. Specifically, a fine wire through a lumen in the wall of the sheath could be used to engage a structure near the distal end of the stent delivery catheter to secure the distal end of the sheath to a distal section of the stent delivery catheter. Such a wire could then be pulled back to release the sheath from the stent delivery catheter. Another method for securing the distal end of the sheath to a distal section of the stent delivery catheter would be to have threads at the sheath's distal end that screw into a fitting on a distal section of the stent delivery catheter. Then the sheath could be released by unscrewing it from the stent delivery catheter by rotating the sheath relative to the stent delivery catheter at their proximal ends that lie outside the patient's body. Thus, it should be understood that the invention disclosed herein is any stent delivery catheter system that has a sheath that is releasably attached to a distal section of a stent delivery catheter. This attachment of the sheath to the stent delivery catheter could even be located just proximal to the proximal end of the stent with some sheath extending in the distal direction to cover the stent.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery catheter system for placing a stent within a vessel of a human body, the system comprising:
   a flexible guide wire;
   a stent delivery catheter having a distal section which includes a radially expandable metal stent, the stent delivery catheter also having a central lumen through which the guide wire can be slideably placed;
   a sheath having a distal end and having at least one tab located at its distal end, the sheath being coaxially and slideably placed around the stent delivery catheter; and
   the at least one tab of the sheath being releasably attached by the guide wire to a fitting located at the distal section of the stent delivery catheter.

2. The invention of claim 1 wherein there are two tabs.

3. The invention of claim 1 wherein there is at least one hole in the tab through which the guide wire can be passed.

4. The invention of claim 1 wherein the fitting at the distal section of the stent delivery catheter has at least one slot into which the tab can be inserted.

5. The invention of claim 4 wherein there are two slots.

6. The invention of claim 1 wherein the stent delivery catheter uses an inflatable balloon to deploy the stent.

7. The invention of claim 1 wherein the stent is self-expanding.

8. A stent delivery catheter system for placing a stent within a vessel of a human body, the system comprising:
   a flexible guide wire;
   a stent delivery catheter system having a distal section which includes a radially expandable metal stent, the stent delivery catheter also having a central lumen through which the guide wire can be slideably placed;
   a slidable sheath covering the stent, the sheath having a distal end which is releasably attached by the guide wire to the distal section of the stent delivery catheter.

9. A method for placing a stent within a stenosed blood vessel of the human body, the method comprising the following steps:

(a) placing a flexible guide wire having a distal end through the vascular system of the human body until the guide wire's distal end lies distal to the vessel stenosis;

(b) advancing a stent delivery catheter system over the guide wire which stent delivery catheter system includes a stent delivery catheter having a distal section, a stent located at said distal section of the stent delivery catheter and a sheath that is coaxially and slideably mounted around the stent delivery catheter, the sheath having at least one tab at its distal end which tab has a central hole through which the guide wire can pass, the at least one tab being placed into a fitting at the distal end of the stent delivery catheter;

(c) continuing to advance the stent delivery catheter system until the stent located at the distal end of the stent delivery catheter is situated at the site of the vessel stenosis;

(d) pulling back the guide wire until its distal end lies proximal to the at least one tab of the sheath;

(e) pulling back the sheath relative to the stent delivery catheter until the stent is uncovered; and (f) deploying the stent at the site of the vessel stenosis.

10. The method of claim 9 wherein the stent is a balloon expandable stent and the stent delivery catheter is a balloon angioplasty catheter having an inflatable balloon at the distal section of the stent delivery catheter and the stent is deployed to open the vessel obstruction by inflating the balloon.

11. The method of claim 10 further including the step of deflating the balloon and removing the stent delivery catheter and sheath from the human body.

12. The method of claim 9 wherein the stent is a self-expanding stent which automatically deploys radially outward against the wall of the vessel after the sheath is pulled back.

13. A method for placing a stent within a stenosed blood vessel of the human body, the method comprising the following steps:

(a) placing a flexible guide wire having a distal end through the vascular system of the human body until the guide wire's distal end lies distal to the vessel stenosis;

(b) advancing a stent delivery catheter system over the guide wire which stent delivery catheter system includes a stent delivery catheter having a distal section, a radially expandable metal stent located at said distal section of the stent delivery catheter and a sheath that is coaxially and slideably mounted around the stent delivery catheter, the distal end of the sheath being releasably attached by the guide wire to the distal section of the stem delivery catheter;

(c) continuing to advance the stent delivery catheter system until the stent located at the distal end of the stent delivery catheter is situated at the site of the vessel stenosis;

(d) detaching the distal end of the sheath from the distal section of the stent delivery catheter;

(e) pulling back the sheath relative to the stent delivery catheter until the stent is uncovered; and (f) deploying the stent at the site of the vessel stenosis.

* * * * *